United States Patent
Goldberg et al.

(10) Patent No.: US 7,106,895 B1
(45) Date of Patent: Sep. 12, 2006

(54) METHOD AND APPARATUS FOR INSPECTING RETICLES IMPLEMENTING PARALLEL PROCESSING

(75) Inventors: Edward M. Goldberg, Sunnyvale, CA (US); Erik N. Johnson, Santa Clara, CA (US); Lawrence R. Miller, Pleasanton, CA (US)

(73) Assignee: KLA-Tencor, San Jose, CA (US)

( * ) Notice: Subject to any disclaimer, the term of this patent is extended or adjusted under 35 U.S.C. 154(b) by 0 days.

(21) Appl. No.: 09/449,022

(22) Filed: Nov. 24, 1999

(51) Int. Cl.
*G06K 9/00* (2006.01)

(52) U.S. Cl. ...................................... 382/144; 382/145
(58) Field of Classification Search ........ 382/144–147, 382/149, 141; 348/126; 712/28, 31; 709/201, 709/208; 345/505
See application file for complete search history.

(56) References Cited

U.S. PATENT DOCUMENTS

| | | | | |
|---|---|---|---|---|
| 3,887,762 A | 6/1975 | Uno et al. | ...................... | 178/6 |
| 4,181,936 A * | 1/1980 | Kober | ........................ | 709/212 |
| 4,253,112 A | 2/1981 | Doemens | .................... | 358/101 |
| 4,445,137 A * | 4/1984 | Panofsky | .................... | 382/302 |
| 4,484,081 A | 11/1984 | Cornyn et al. | ............... | 250/563 |
| 4,484,349 A * | 11/1984 | McCubbrey | ................ | 382/308 |
| 4,589,140 A | 5/1986 | Bishop et al. | ................. | 382/8 |
| 4,953,224 A | 8/1990 | Ichinose et al. | ............... | 382/8 |
| 4,979,223 A | 12/1990 | Manns et al. | .................. | 382/8 |
| 4,984,282 A | 1/1991 | Manns et al. | .................. | 382/8 |
| 4,985,927 A | 1/1991 | Norwood et al. | ............... | 382/8 |
| 4,999,785 A | 3/1991 | Schmuter | ..................... | 364/507 |
| 5,001,764 A | 3/1991 | Wood et al. | .................... | 382/8 |
| 5,018,212 A | 5/1991 | Manns et al. | .................. | 382/8 |
| 5,046,110 A | 9/1991 | Carucci et al. | ................. | 382/8 |
| 5,095,447 A | 3/1992 | Manns et al. | ................ | 395/161 |
| 5,119,434 A | 6/1992 | Bishop et al. | ................. | 382/8 |
| 5,357,632 A * | 10/1994 | Pian et al. | ..................... | 707/4 |
| 5,495,337 A | 2/1996 | Goshorn et al. | ............ | 356/376 |
| 5,517,234 A | 5/1996 | Gerber et al. | ............... | 348/126 |
| 5,537,669 A | 7/1996 | Evans et al. | ................ | 382/141 |
| 5,608,453 A | 3/1997 | Gerber et al. | ................. | 348/87 |
| 5,621,811 A | 4/1997 | Roder et al. | ................ | 382/147 |
| 5,659,630 A | 8/1997 | Forslund et al. | ............ | 382/149 |
| 6,081,659 A * | 6/2000 | Garza et al. | ................ | 382/144 |

FOREIGN PATENT DOCUMENTS

WO     WO 98/01827     1/1998

* cited by examiner

*Primary Examiner*—Vikkram Bali
*Assistant Examiner*—Colin LaRose
(74) *Attorney, Agent, or Firm*—Beyer Weaver & Thomas, LLP

(57) ABSTRACT

Disclosed is an apparatus for analyzing a plurality of image portions of at least a region of a sample. The apparatus includes a plurality of processors arranged to receive and analyze at least one of the image portions, and the processors being arranged to operate in parallel. The apparatus also includes a data distribution system arranged to receive image data, select at least a first processor for receiving a first image from the image data, select at least a second processor for receiving a second image from the image data, and output the first and second image portions to their selected processors.

45 Claims, 8 Drawing Sheets

US 7,106,895 B1

METHOD AND APPARATUS FOR INSPECTING RETICLES IMPLEMENTING PARALLEL PROCESSING

CROSS REFERENCES TO RELATED APPLICATIONS

This application is related to U.S. patent application filed on 7 Apr. 1998 having issue number U.S. Pat. No. 5,737,072, entitled "Automated Photomask Inspection Apparatus and Method" by Emery et al., U.S. patent application filed on 17 Dec. 1998 having application Ser. No. 09/213,744, entitled "Mechanisms for Making and Inspecting Reticles" by Glasser et al., and U.S. patent application filed on 18 Dec. 1997, having application Ser. No. 08/993,107, entitled "Method for Inspecting a Reticle" by Bareket et al., which applications are herein incorporated by reference in their entirety.

BACKGROUND OF THE INVENTION

The present invention relates generally to apparatus and techniques for inspecting a sample, such as a reticle, photomask, or other semiconductor materials or surfaces, and more specifically to apparatus and methods for determining whether a sample is defective.

A reticle or photomask is an optical element containing transparent and opaque, semi-transparent, and phase shifting regions which together define the pattern of coplanar features in an electronic device such as an integrated circuit. Reticles are used during photolithography to define specified regions of a semiconductor wafer for etching, ion implantation, or other fabrication process. For many modern integrated circuit designs, an optical reticle's features are between about 1 and about 5 times larger than the corresponding features on the wafer. For other exposure systems (e.g., x-ray, e-beam, and extreme ultraviolet) a similar range of reduction ratios also apply.

Optical reticles are typically made from a transparent medium such as a borosilicate glass or quartz plate on which is deposited on an opaque and/or semi-opaque layer of chromium or other suitable material. However, other mask technologies are employed for direct e-beam exposure (e.g., stencil masks), x-ray exposure (e.g., absorber masks), etc. The reticle pattern may be created by a laser or an e-beam direct write technique, for example, both of which are widely used in the art.

After fabrication of each reticle or group of reticles, each reticle is typically inspected by illuminating it with light emanating from a controlled illuminator. Optical images of one or more portions of the reticle are constructed based on the fraction of the light reflected, transmitted, or otherwise directed to a light sensor. Such inspection techniques and apparatus are well known in the art and are embodied in various commercial products such as many of those available from KLA-Tencor Corporation of San Jose, Calif.

During a conventional inspection process, the optical image of the reticle portion being inspected is typically compared to a corresponding reference image. Conventionally, the reference image is either generated from a circuit pattern data that was used to fabricate the reticle or from an optical image of a nearby area of the reticle itself. Either way, the optical image features are analyzed and compared with corresponding features of the reference image. Each feature difference is then typically compared against a threshold value. If the optical image feature varies from the test feature by more than the predetermined threshold, a defect is defined.

Mechanisms for a typical inspection process may include a number of serially coupled processors. The image data is fed into and processed by a first processor. After the first processor performs one step of the analysis, the resultant data is then fed into a second processor for the next step in the analysis. The image data may be fed serially into any number of processors. Typically, the different processors will each perform some small portion of the total analysis algorithm(s). The algorithms are usually hard-coded into the individual processors.

Although serially processing portions of the image data is adequate for some applications; it is too slow and/or inflexible under certain conditions. For example, as circuit patterns and corresponding reticle patterns grow more complex, the image data of such reticles grows to contain a relatively large amount of data that must be accurately analyzed. A typical reticle may be converted into 1 million by 1 million pixels of image data. Thus, it may become quite burdensome to process such large amounts of image data.

Additionally, conventional image processing is often dependent on the proper functioning of all of the processors. That is, if a single processor fails within the serial chain of processors, the image data may not be properly analyzed. The inability to properly analyze is especially likely if there are no other processors within the serial chain of processors that perform the failed processor's functions.

Finally, inspection systems that include processors with fixed or hard-coded algorithms often cannot handle the full range of possible algorithms that may be useful for image processing, and they are not easily upgraded or changed if a new set of algorithms is desired. For example, if new algorithms are desired, the processors may have to be replaced with new processors that have a new set of hard-coded algorithms. This procedure may be relatively time-consuming and/or costly.

Thus, improved inspection apparatus and techniques are needed. More specifically, mechanisms for more efficiently and accurately processing image data are desired. Additionally, flexible mechanisms for changing the processor algorithms are also desirable.

SUMMARY OF THE INVENTION

Accordingly, the present invention addresses the above problems by providing apparatus and methods for analyzing multiple images or image portions of a sample. In general terms, the sample is divisible into a plurality of patches. Each image corresponds to a patch of the sample and is routed to one or more processors. The processors are configured to operate in parallel and to implement various algorithms on the received images. Several processors may simultaneously analyze the same or different images (that correspond to the same or different patches of the sample) with the same or different algorithms.

In one embodiment, an apparatus for analyzing a plurality of image portions of at least a region of a sample is disclosed. The apparatus includes a plurality of processors arranged to receive and analyze at least one of the image portions, and the processors are arranged to operate in parallel. The apparatus also includes a data distribution system arranged to receive image data, select at least a first processor for receiving a first image portion of the image data, select at least a second processor for receiving a second image portion of the image data, and output the first and second image portions to their selected processors.

In another aspect of the invention, the first processor is arranged to receive a first reference image portion corresponding to the first image portion and to compare the first image portion to the first reference image portion, and the second processor is arranged to receive a second reference image portion corresponding to the second image portion and to compare the second image portion to the second reference image portion.

In another aspect, the first processor is arranged to receive a first reference data portion that characterizes a pattern in the sample that the first image portion corresponds to, and the first processor is also arranged to render the first reference data portion to a first reference image portion and to compare the first reference image portion to the first image portion.

In an alternative embodiment, an apparatus for inspecting a plurality of image portions of at least a region of a sample is disclosed. The apparatus includes a plurality of distributors arranged to receive the image portions and a plurality of processors that are arranged into a plurality of subgroups that are each coupled to an associated distributor. Each distributor is configurable to output selected image portions to its associated subgroup of processors, and at least two of the processors are arranged to analyze at least two of the image portions in parallel.

In a preferred embodiment, each subgroup of processors includes a supervisor processor that is coupled with an associated one of the distributors so as to receive the selected image portions from the associated distributor, wherein each supervisor processor is configurable to distribute the selected image portions to selected processors within its associated subgroup.

In yet another embodiment, a method of inspecting a sample having a plurality of fine patterns thereon and processing data resulting from the inspection is disclosed. Data derived from the inspection in a multiprocessor system is received. The system includes a master processor and a plurality of slave processors. The data is divided into groups using the master processor. Each group of data corresponds to information derived from a portion of the sample, and each group has a quantity of data which may be processed by a slave processor in a predetermined time interval. The data groups are processed with the slave processors, and defect information regarding the sample and the fine patterns is derived from the combined data.

In an alternative embodiment, a method for analyzing image data obtained from a sample using a plurality of processors is disclosed. Image data from an inspection system that generates the image data from a sample is received. The image data is divided into a plurality of image portions that correspond to various portions of the sample. Each image portion is output to a selected processor with each image portion going to a different processor. Each image portion is analyzed for defects within the selected processor. Results from each processor are output and combined such that defect data is compiled for the entire image data.

In yet another embodiment, a computer readable medium containing program instructions for inspecting a sample having a plurality of fine patterns thereon, and processing data resulting from the inspection is disclosed. The computer readable medium includes computer readable code for (i) receiving data derived from the inspection in a multiprocessor system, wherein the system includes a master processor and a plurality of slave processors, (ii) dividing the data into groups using the master processor, wherein each group corresponds to information derived from a portion of the sample and each group has a quantity of data which may be processed by a slave processor in a predetermined time interval, (iii) processing the data groups with the slave processors, and (iv) deriving defect information regarding the sample and the fine patterns from the combined data, as well as a computer readable medium for storing the computer readable codes.

In another embodiment, a computer readable medium containing program instructions for inspecting a sample having a plurality of fine patterns thereon, and processing data resulting from the inspection is disclosed. The computer readable medium includes computer readable code for (i) receiving image data from an inspection system that generates the image data from a sample, (ii) dividing the image data into a plurality of image portions that correspond to various portions of the sample, (iii) outputting each image portion to a selected processor, wherein at least some of the image portions go to different processors, (iv) analyzing each image portion for defects within the selected processor, and (v) outputting and combining results from each processor such that defect data is compiled for the entire image data; as well as a computer readable medium for storing the computer readable codes.

These and other features and advantages of the present invention will be presented in more detail in the following specification of the invention and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF SPECIFIC EMBODIMENTS

Reference will now be made in detail to the specific embodiments of the invention. Examples of the these specific embodiments are illustrated in the accompanying drawings. While the invention will be described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
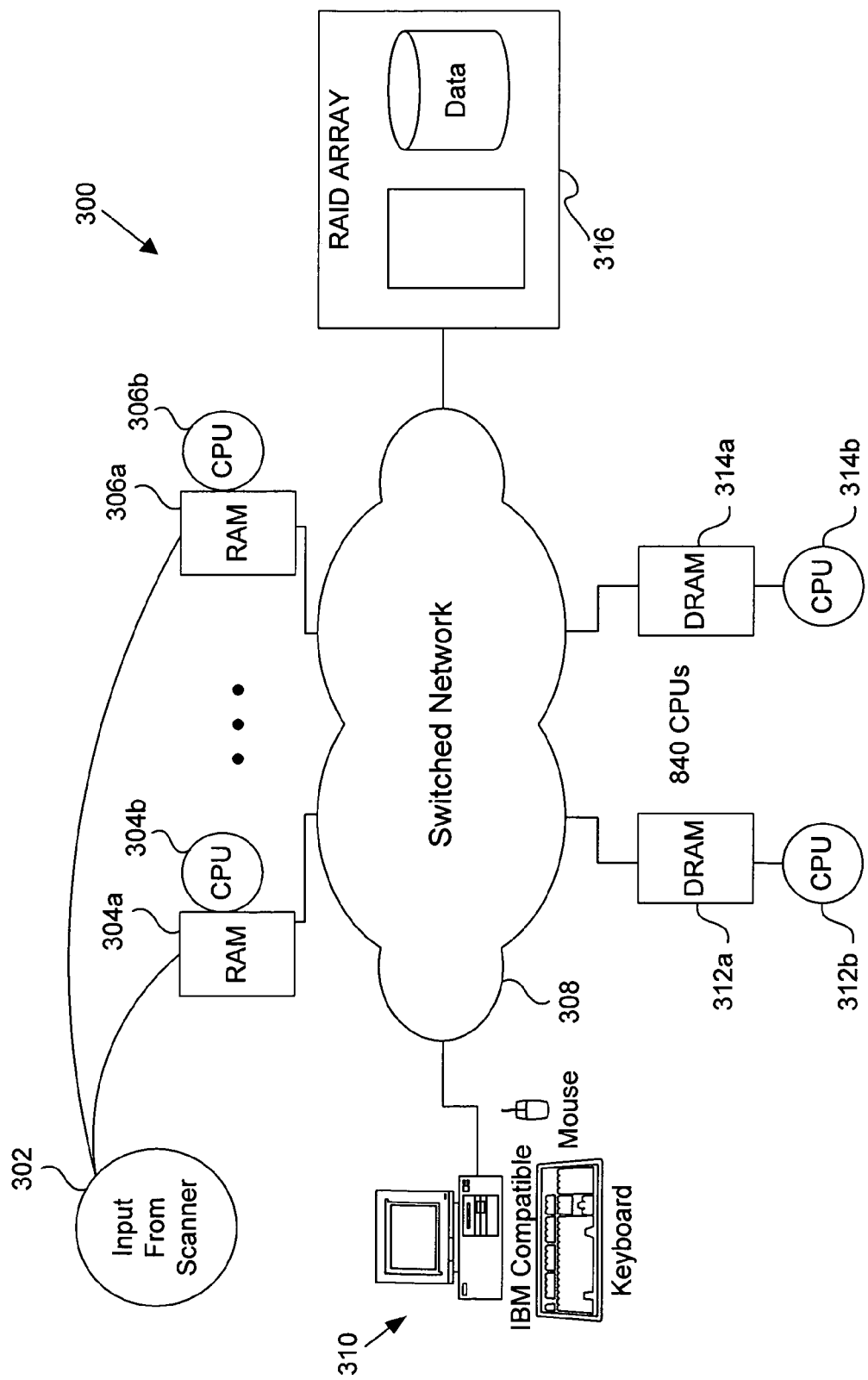
FIG. 1 is a diagrammatic representation of an inspection system in accordance with one embodiment of the present invention.

FIG. 1 is a diagrammatic representation of an inspection system 300 in accordance with one embodiment of the present invention. The inspection system includes input 302 from a scanner (not shown), a data distribution system 308, a group of processors (e.g. 312 and 314), an optional mass storage device 316, and a system control processor 310. A processor typically may include one or more microprocessor integrated circuits and may also contain interface and/or memory integrated circuits and may additionally be coupled to one or more shared and/or global memory devices. These processors are also referred to as "leaf processors."

Data distribution system 308 is arranged to receive input 302 from a scanner or data acquisition system (not shown). The scanner may be any suitable instrument for obtaining an image of a sample. For example, the scanner may construct an optical image of a portion of the sample based on a portion of light that is reflected, transmitted, or otherwise directed to one or more light sensors. Alternatively, the scanner may utilize an electron beam (e-beam), or other methods, for obtaining an image of the sample.

The image data may be obtained from any suitable sample type. That is, the sample may be anything that results in a relatively large amount of image data. For example, the sample may be a reticle having a multitude of fine patterns thereon. By way of another example, the sample may be a semiconductor device or material, a backside pellicle, or a computer disk.

The image data 302 may take any suitable form for representing an image of the sample. For example, the image data typically includes a plurality of images or image portions that each represent a portion or patch of the sample. The portions of the sample are scanned to create image data. These sample portions and corresponding images may be any size and shape, depending on the particular system and application requirements. The images may be obtained by scanning the sample in any suitable manner. By way of example, the images may be obtained by raster scanning the sample. Alternatively, the images may be obtained by scanning the sample with any suitable pattern, such as a circular or spiral pattern. Of course, the sensors may have to be arranged differently (e.g., in a circular pattern) and/or the sample may be moved differently (e.g., rotated) during scanning in order to scan a circular or spiral shape from the sample.

In the embodiment illustrated below, as the sample moves past the sensors, a rectangular region (herein referred to as a "swath") of the sample is converted into a set of images. In this embodiment, the sensors of the scanner are arranged in a rectangular pattern. For this example, the sensors are arranged to receive light from the sample and generate therefrom a set of data that corresponds to a swath of the sample, which is about 1 million pixels wide and about 1000 to 2000 pixels high.

Figure 2:
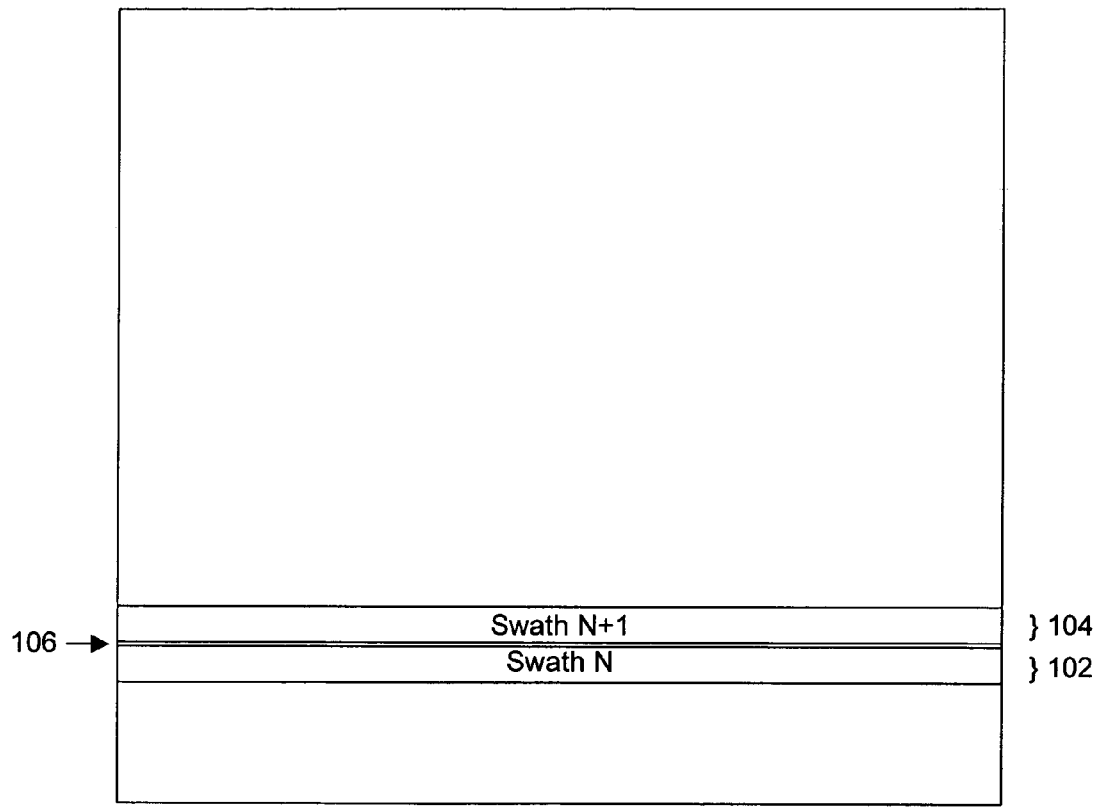
FIG. 2 is a diagrammatic representation of two sets of image data corresponding to two "swaths" of a sample, such as a reticle, in accordance with embodiment of the present invention.
Figure 2:
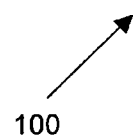

FIG. 2 is a diagrammatic representation of two sets of image data corresponding to two "swaths" 102 and 104 of a sample 100, such as a reticle, in accordance with embodiment of the present invention. Each set of image data may correspond to a "swath" of the sample 100. In the example of FIG. 2, a first set of image data corresponds to a first swath 102 of the sample 100, and a second set of image data corresponds to a second swath 104 of the sample 100.

Each set of image data may be obtained by sequentially scanning swaths from the sample in a serpentine or raster pattern. For example, the first swath 102 of the sample 100 is scanned by an image acquisition system from left to right to obtain a first set of image data. The second swath 104 is then scanned from right to left to obtain a second set of image data.

In a preferred embodiment, there is an overlap 106 between each set of image data and the next set of image data that corresponds to an overlap on the sample. This overlap allows more flexibility in processing certain patterns on the sample 100. For example, this overlap ensures that any pattern anywhere on the part of the surface covered by overlapping swaths will be full contained within at least one swath, as long as the height of the pattern is less than or equal to the height of the overlap area. Most algorithms cannot properly detect a defect in a pattern unless the whole pattern is present in the image portion that the algorithm is examining.

Turning back to FIG. 1, the image data 302 is received by data distribution system 308. The data distribution system 308 may be associated with one or more memory devices, such as RAM buffers, for holding at least a portion of the received image data 302. Preferably, the total memory is large enough to hold an entire swatch of image data. For example, one gigabyte of memory works well for a swatch that is 1 million by 1000 pixels.

The data distribution system 308 also controls distribution of portions of the received image input data 302 to the leaf processors (e.g. 312 and 314). For example, data distribution system 308 may route a first image to leaf processor 312, and may route a second image to leaf processor 314.

The leaf processors may receive an image that corresponds to at least a portion or patch of the sample. The leaf processors may each also be coupled to or integrated with one or more memory devices (not shown), such as DRAM devices that provide local memory functions, such as holding the image data portion. Preferably, the memory is large enough to hold an image that corresponds to a patch of the sample. For example, eight megabytes of memory works well for an image corresponding to a patch that is 512 by 1024 pixels. Alternatively, the leaf processors may share memory.

Each set of image data 302 may correspond to a swath of the sample. One or more sets of image data may be stored in memory of the data distribution system 308. This memory may be controlled by one or more processors within the data distribution system 308, and the memory may be divided into a plurality of partitions. For example, the data distribution system 308 may receive an image corresponding to a portion of a swath into a first memory partition (not shown), and the data distribution system 308 may receive another image corresponding to another swath into a second memory partition (not shown). Preferably, each of the memory partitions of the data distribution system 308 only holds the portions of the image data that are to be routed to a processor associated with such memory partition. For example, the first memory partition of the data distribution system 308 may hold and route a first image to processor 312, and the second memory partition may hold and route a second image to processor 314.

Figure 3:
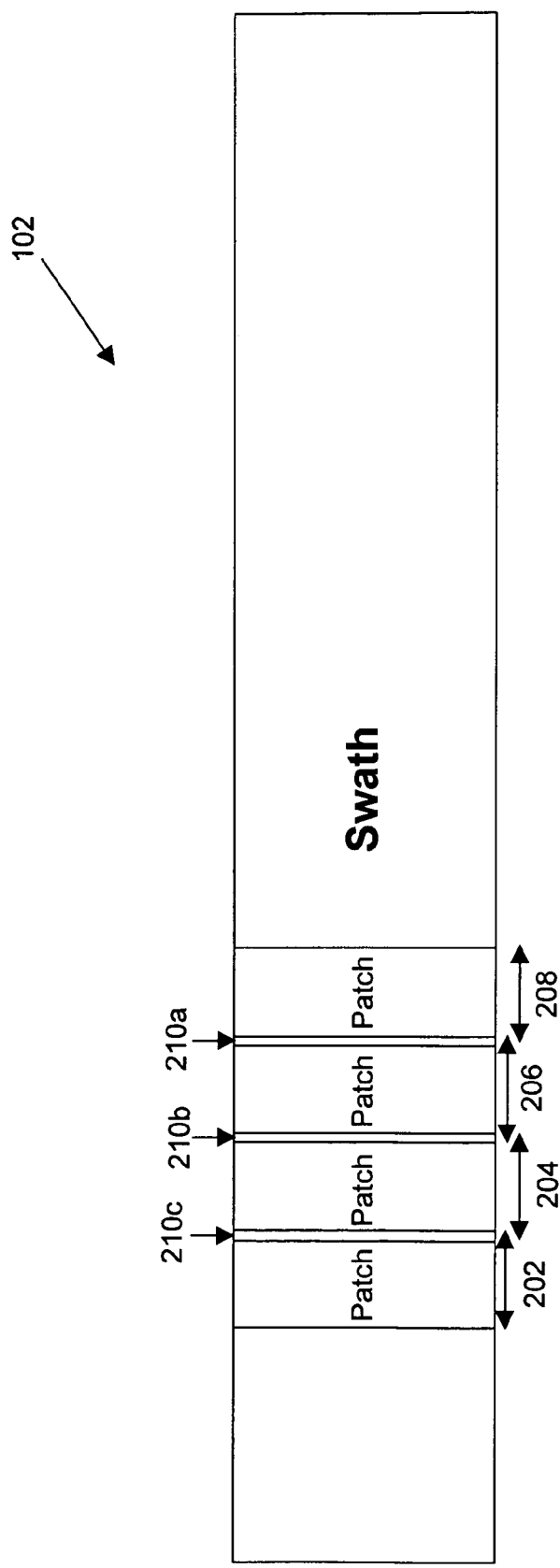
FIG. 3 is a diagrammatic illustration of images that correspond to a swath that is divided into patches in accordance with one embodiment of the present invention.

The data distribution system 308 may also divide and route portions of the received image data to processors. The image data may be divided by the data distribution system 308 in any suitable manner for facilitating data analysis. For example, the image data may be divided into images that each correspond to a "patch" of the sample. FIG. 3 is a diagrammatic illustration of an image data set 102 that corresponds to a swath that is divided into patches in accordance with one embodiment of the present invention.

As shown, the image set 102 includes a plurality of images 202, 204, 206, and 208, and each image corresponds to patch of a sample. Like the sets of image data corresponding to overlapping swaths, the images within a particular set of image data may also overlap. As shown, there is an overlap area 210c between images 202 and 204, an overlap area 210b between images 204 and 206, and an overlap area 210a between images 206 and 208.

As discussed above for the overlapping swath images of FIG. 2, overlapping of patch images also facilitates reliable processing. For example, the overlapping areas make it possible to process a complete structure that lies partly or completely within the overlap area when the width of the structure is less than the overlap width. The erosion or loss of data that occurs at the edges of patches when using convolutions and other local-neighborhood operations can also be eliminated when there is an overlap.

Additionally, the overlap areas may allow for independent functioning of the processors. In other words, each processor may independently analyze an image without having to share information with another processor. The overlap areas can eliminate the need for leaf processors to communicate with each other, which results in a simpler architecture. For example, the memory partition containing the image data may be read-only accessible by the leaf processor, and thus, mechanisms for ensuring cache coherency are not required.

The data distribution system 308 may define and distribute each image of the image data based on any suitable parameters of the image data. For example, the images may be defined and distributed based on the corresponding position of the patch on the sample. In one embodiment, each swath is associated with a range of column positions that correspond to horizontal positions of pixels within the swath. For example, columns 0 through 256 of the swath may correspond to a first patch, and the pixels within these columns will comprise the first image, which is routed to one or more leaf processors. Likewise, columns 257 through 512 of the swath may correspond to a second patch, and the pixels in these columns will comprise the second image, which is routed to different leaf processor(s).

In sum, the present invention provides mechanisms for dividing the image data into manageable chunks or image portions that may be readily analyzed in parallel by individual leaf processors. Thus, the entire image data may be parsed into a number of images, and one or more image(s) may be distributed to each separate leaf processor. The leaf processors may then independently, efficiently analyze the received images(s) in parallel.

After one of the leaf processors receives an image, it is analyzed in any suitable manner so as to derive information about the received image input 302. In one embodiment, the processor may also receive reference data from database 316, in addition to the image. This reference data may be in any suitable form that facilitates characterization of the image input data 302. For example, the reference data may be generated from a provided circuit pattern design database (e.g., that resides in mass storage 316). The reference data may be received as a grayscale pixel-mapped reference image, or it may be received as a specification of a set of shapes and their locations that together define the reference pattern. In the latter case, the leaf processor converts the reference data to a grayscale pixel-mapped reference image before comparing the reference information with the image portion.

The reference data may be processed by the leaf processor in any suitable manner, such as by directly converting the contents of the circuit pattern database into a reference image. The reference data portion (e.g., from the circuit pattern database) may be converted or rendered into a reference image portion by the leaf processors in a way that takes into account the effects of fabrication and image acquisition processes. For example, the corners of a circuit pattern in the reference data may be rounded during conversion to simulate the corner rounding that commonly occurs during fabrication of a reticle. The rendered reference image may also be adjusted to simulate expected optical effects of the optical image acquisition system. Such optical effects are necessarily encountered when an optical inspection technique is used to evaluate a reticle.

Thus, the reference image may represent what the image of the patch should look like without any defects. By way of specific example, leaf processor 312 may be configured to receive a first image of the image data 302 and corresponding reference data 316. Additionally, leaf processor 312 may generate the corresponding reference image from the reference data. The leaf processor 312 may then compare are the first image to the corresponding reference image 316. If leaf processor 312 determines that there are relatively large differences, in degree and/or kind, between the image and reference image, the leaf processor 312 may define, report, and/or flag one or more defects for the patch corresponding to the image.

Alternatively, the reference data may be an image corresponding to a patch of the sample that is within a die adjacent to the die of the patch under test. This is commonly referred to as a die-to-die analysis. In other words, images corresponding to two adjacent die patches are analyzed in conjunction by a leaf processor. The present invention may also be implemented for cell-to-cell comparisons. By way of another example, an image that is generated with light reflected off the sample may be compared with an image that is generated with light transmitted through the sample. Several embodiments of this technique are described in U.S. patent application filed on 7 Apr. 1998 having issue number U.S. Pat. No. 5,737,072, entitled "Automated Photomask Inspection Apparatus and Method" by Emery et al., which is herein incorporated by reference in its entirety. By way of a final example, the reference data may be in the form of previously obtained image data before any defects were present on the sample. Several embodiment are described in U.S. patent application filed on 18 Dec. 1997, having application Ser. No. 08/993,107, entitled "Method for Inspecting a Reticle" by Bareket et al., which is herein incorporated by reference in its entirety.

Any suitable algorithms may be implemented for analysis of an image. For example, an algorithm may simply compare line widths between the image and reference data. If the difference between the width of a line in the image and a width of a line in the reference image is more than a predetermined amount, a defect may be flagged by the leaf processor. The same algorithm may be used by two different leaf processors, but under varying conditions. For example, the predetermined amount may be less stringent for one leaf processor and more stringent for the other leaf processor. In sum, the algorithms used by the individual leaf processors may vary qualitatively and/or quantitatively. Several embodiments for various algorithms and inspection analysis techniques are described in U.S. patent application issued on Mar. 4, 2003 having U.S. Pat. No. 6,529,621, entitled "Mechanisms for Making and Inspecting Reticle" by Glasser et al., which is herein incorporated by reference in its entirety.

As shown in FIG. 1, the inspection system 300 also includes central processor 310 for providing a user interface and controlling the various components of the inspection system 300. The central processor 310 may take any suitable form for interfacing with and controlling the inspection system components. The central processor 310 may in the form of an IBM compatible computer, for example, that communicates with the components that are coupled with the data distribution system 308. The central processor 310 may be used to configure the data distribution system 308 to divide, store and/or distribute particular portions of the image input 302 to particular processors (e.g. 312 and 314). For example, data distribution system 308 may be configured to distribute a first portion of the image data 302 to processor 312. Similarly, data distribution system 308 may be configured to distribute a second portion of the image data 302 to processor 314.

The central computer 310 may also be utilized to configure how processors analyzes the received portions of the image data 302. For example, each processor may be configured to implement a different algorithm for processing its received portion of image data 302. By way of another example, each processor may use the same algorithm, but be configured to implement the algorithm under different conditions.

Although the processors of the present invention are described as being configurable by a central processor or computer, of course, the processors may contain hard-coded instructions. However, when the processors are configurable, the present invention provides a flexible and efficient system for inspecting samples. That is, algorithms may be carefully tailored and changed on the fly for different sample types, different patches on the sample, and different application requirements.

FIG. 1 is a conceptual representation of the present invention. Thus, some components that may be implemented within the inspection system 300 have been excluded from the illustration so as to not obscure the invention. Additionally, the particular arrangement of the various components of the inspection system 300 is merely illustrative and not intended to limit the scope of the present invention.

Figure 4:
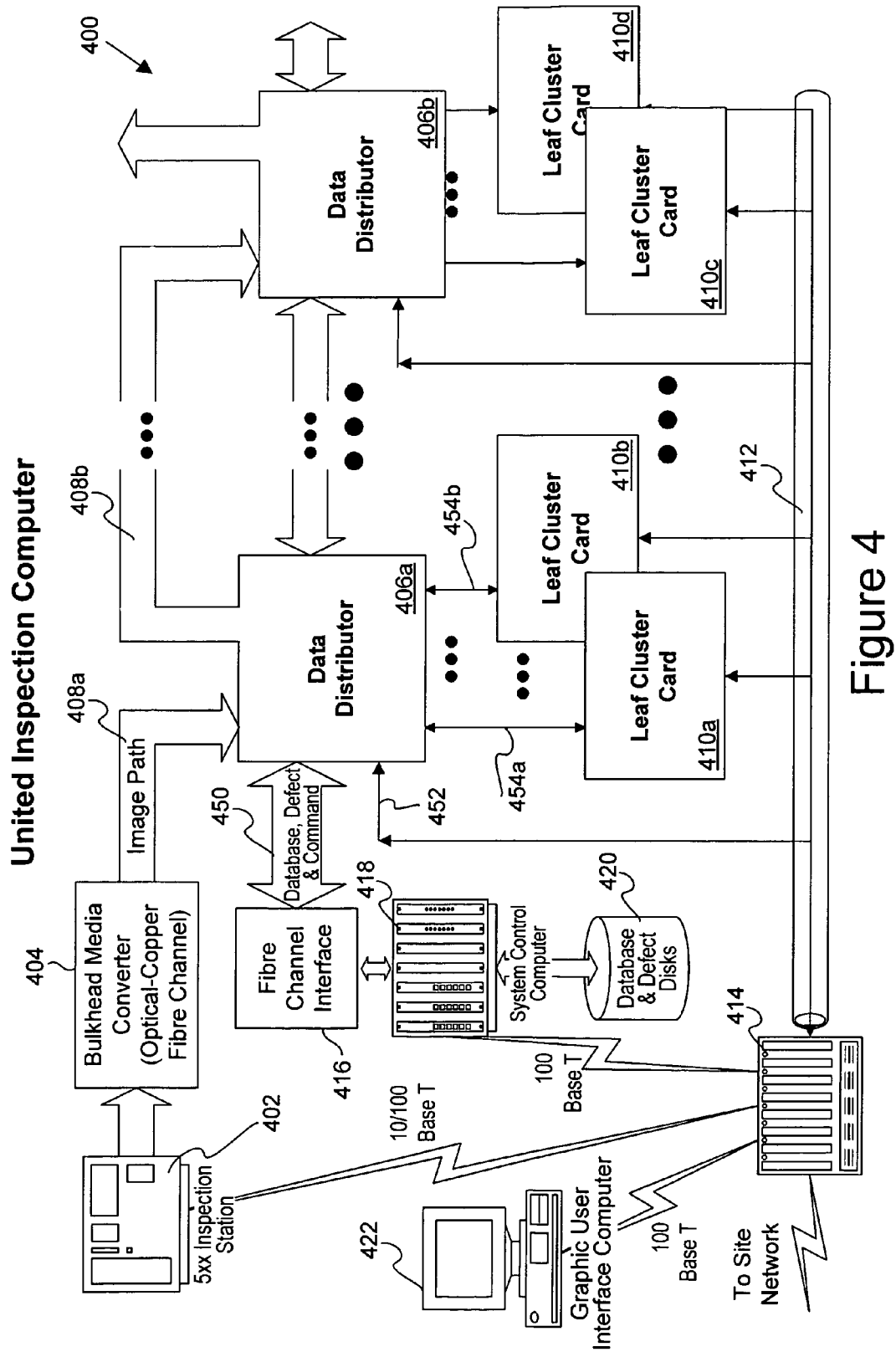
FIG. 4 is a detailed diagrammatic representation of an inspection system in accordance with one embodiment of the present invention.

FIG. 4 is a detailed diagrammatic representation of an inspection system 400 in accordance with one embodiment of the present invention. The inspection system 400 receives image data from an image acquisition system 402. The inspection system 400 includes an image data interface 404, a plurality of data distributors 406, a plurality of leaf cluster cards 410 for each data distributor, a database and control interface 416, a system control processor 418, a database storage device 420, a switch 414, network bus 412, and a user interface 422.

The image acquisition system 402 is configured to obtain image data from a sample. For example, the image acquisition system 402 scans the sample to generate pixel data and thereby extracts the image data. In general terms, the image data represents a path of a sensor of the inspection station as it travels across the sample (or rather, as the sample moves under the sensor) and acquires image data. In one embodiment, image data of a swath is obtained. For example, the image data may be one million pixel wide by one thousand to two thousand pixels. A typical reticle may be converted into an image of one million by one million pixels, and requires five hundred to one thousand sets of image data that each correspond to a swath.

The image data interface 404 formats the received image data from the image acquisition system 402 into data signals that may be received and processed by the inspection system 400 components. For example, the image data interface 404 converts fiber optic signals from the inspection station to copper wire signals that represent the image data. The converted image data is fed into one or more of the data distributors 406. As shown, the image data interface 404 outputs this converted image data 408*a* to a first data distributor 406*a*. Of course, image data interface 404 is not required if the image acquisition system 402 and inspection system 400 utilize the same signal format.

In one embodiment, the data distributors 406 are coupled together in a "daisy chain" configuration. As shown, the first data distributor receives the image data 408*a* and outputs the image data 408*b* to another data distributor. Preferably, an entire image data set that corresponds to a swath is seen by each data distributor. Each data distributor receives the image data and outputs it to the next data distributor in the chain. This daisy chain configuration allows easy expansion of the inspection system. That is, data distributors may be coupled to the end of the chain as needed. This configuration does not limit expansion, as compared to a arrangement where the data distributors are all coupled to the image data interface 404 (i.e., the number of data distributors would be limited to the number of physical connections available on the image data interface 404).

The data distributors divide the image data into a plurality of images and route each image to a particular group of processors on one or more leaf cluster card(s) 410. In the illustrated embodiment, each data distributor 406 is coupled with a plurality of leaf cluster cards 410. For example, each data distributor 406 may be coupled to eight leaf cluster cards 410. Each leaf cluster card 410 receives a subset of images of the image data and routes specific images to specific leaf processors within the leaf cluster card itself for further processing and analysis.

Each data distributor 406 may be configured to hold any size of image data, such as an image set that correspond to an entire swath of image data. In this embodiment, each data distributor 406 receives an image set corresponding to the entire swath and partitions it based on any suitable parameters of the image data, such as column position. The data distributors 406 may also each receive reference data from the database 420, and then distribute portions of the reference data to selected leaf cluster cards 410. Alternatively, the reference data may be received directly by the appropriate leaf cluster card 410. Preferably, each data distributor 406 only retains portions of the image set and reference data that will be used by its own lower leaf cluster cards 410.

In one embodiment, a particular data distributor (e.g., 406*a*) stores images for each of its lower leaf cluster cards (e.g., 410*a* through 410*b*). In other words, a group of images is retained from the image data and sent to a particular lower leaf cluster card. By way of example, data distributor 406*a* may retain a first group of images that is routed to leaf cluster card 410a, and retain a second group of images that is routed to leaf cluster card 410b.

In one embodiment, each data distributor 406 determines where to send a subset of images based on position indicators of the image within the image data. For example, the images having a first range of column positions within the image data are routed by a first data distributor 406a to its underlying leaf cluster cards (e.g., 410a and 410b). In contrast, a second data distributor 406b may then send images having a second range of column positions to its underlying leaf cluster card (e.g., 410c and 410d).

Each leaf cluster card 410 receives a subset of images from its associated data distributor 410, and routes specific images within this subset to specific processors residing on the leaf cluster card 410. The individual images are routed to leaf processors on the leaf cluster cards based on a number of factors, such as availability of processor resources. The leaf processors of the leaf cluster cards are configurable for analyzing the received image(s) with various algorithms.

The inspection system 400 may also include database 420 for holding reference data that is utilized by the processors of the leaf cluster cards 410 to analyze the received images. As described above, the reference data may include various types of comparison data, such as expected data, data from an adjacent die or cell, etc. The database storage device may be any suitable storage device for holding large amounts of reference data. For example, the storage may be in the form of a Redundant Array of Independent Disks (referred to as a "RAID array").

In one embodiment, a user interface 422 provides a mechanism for interfacing with and configuring the various components of the inspection system 400. As shown, the system control computer 418 communicates with the data distributor 406 and the leaf cluster cards 410 through a network bus 412 (e.g., an Ethernet bus), as well as communicates with user interface 422.

The system control computer 418 may be coupled to the data distributors 406 in any suitable manner for interfacing with and configuring the various components of the inspection system 400. As shown, the control computer 418 is coupled through a data and control interface 416. Any suitable mechanism for controlling functions of the inspection system 400 may be implemented through the control computer 418. For example, the control computer 418 may allow a user to select and combine particular algorithms and corresponding data into "jobs" that are used to analyze particular images.

Of course, any configuration of processors or computers may be implemented for controlling the components of the inspection system 400. For example, the system control computer 418 and user interface 422 may be integrated into a single computer for interfacing with and controlling the inspection system 400.

Figure 5:
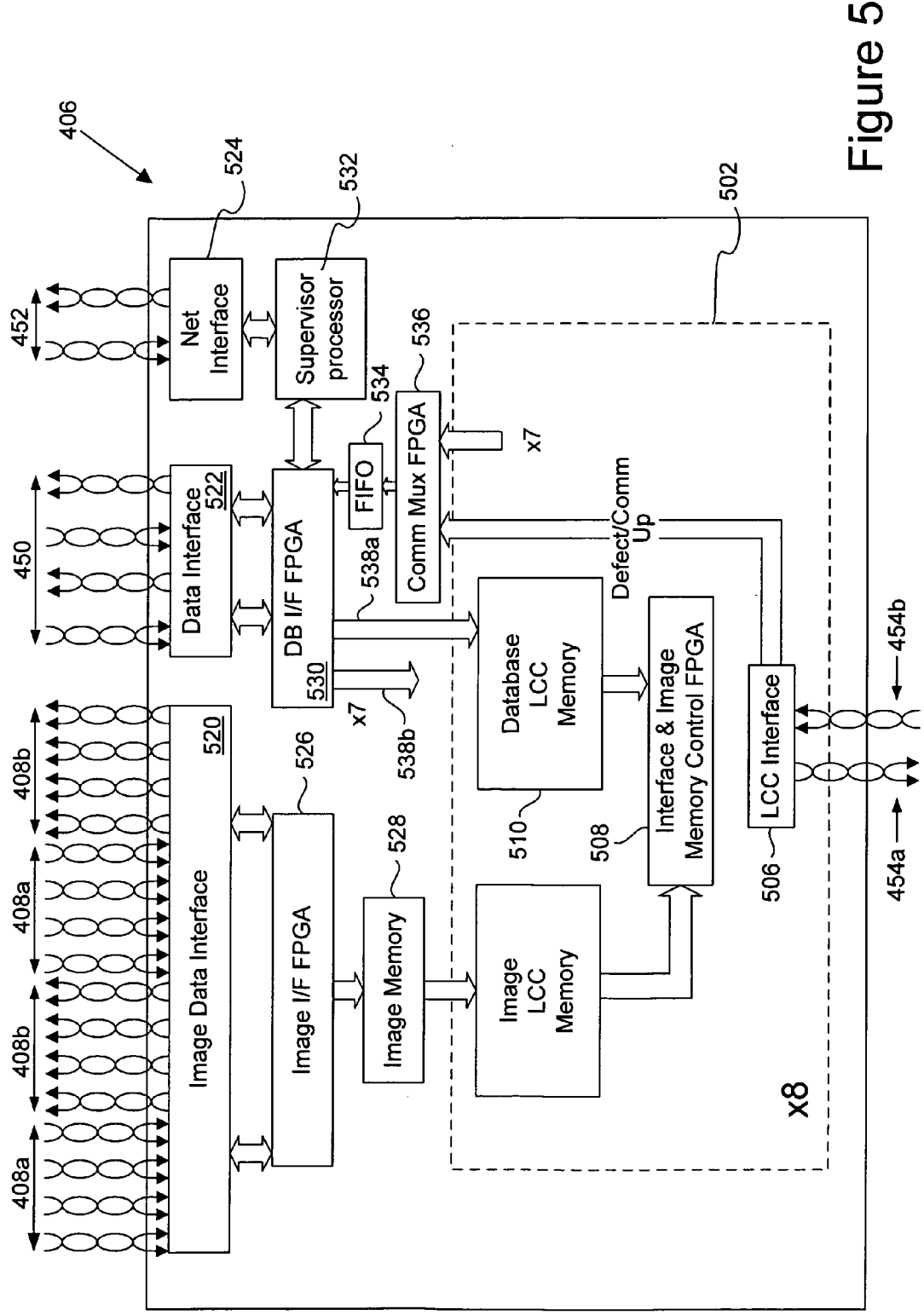
FIG. 5 is a diagrammatic representation of one of the data distributors of FIG. 4 in accordance with one embodiment of the present invention.

FIG. 5 is a diagrammatic representation of one of the data distributors 406 of FIG. 4 in accordance with one embodiment of the present invention. As shown, each data distributor 406 includes image interface 520, database and control interface 522, network interface 524, supervisor processor 532, buffer memories 528 and 510, and a plurality of leaf cluster card (LCC) modules 502.

The data 450a that is required, for example, for image analysis is input into the data distributor 406 from system control computer 418 (see FIG. 4). Data 450a from database 420 may includes reference data corresponding to particular images. Data 450a may also include command and configuration data from user interface processor 422 for controlling the data distributor(s) 406, as well as the leaf cluster card(s) 410. That is, the user may communicate via the user interface 422 with one or more data distributor(s) 406 and leaf cluster card(s) 410.

Similarly, the data distributor 406 may output data 450b through database and control interface 522 to the system control computer 418 and/or the data base 420 through the user interface 422. For example, results data that is generated from analysis of one or more patches may be output through this interface 450b. By way of specific example, the number and/or type of defects may be collected and output as results data.

The network interface 524 may take the form of any suitable mechanism for interfacing with other components of the inspection system, such as the GUI computer 422 (see FIG. 4). For example, the network interface 524 may be in the form of a 100 Base-T Ethernet interface. This network interface 524 may be utilized to program and configure the supervisor processor 532 of the data distributor 406.

The supervisor processor 532 may be configured to implement any suitable number and type of control functions. For example, the supervisor processor 532 may be responsible for initializing other components of the data distributor 406, determining how to divide the received image data into a plurality of images, initializing interrupts for the start and end of a particular swath, determining which images to store within the data distributor memory and forward to its lower leaf cluster cards, and communicating with external devices through the network interface 524. The supervisor processor 532 may also be configured to implement error recovery functions on the received image data.

The supervisor processor 532 may be coupled to local program and data memory (not shown) for facilitating programming. The supervisor processor 532 may take any suitable form for accomplishing the above-mentioned functions. For example, the supervisor processor 532 may take the form of an R5000 processor with internal L1 cache.

The data distributor may include any suitable mechanism for routing data to its underlying leaf cluster cards. In the illustrated embodiment, the image interface 520 may be configured to route specific images to specific lower leaf cluster cards. Likewise, the database and control interface 522 may be configured to route specific reference data to specific leaf cluster cards. The image interface 520 and database and control interface 522 may be programmed via the supervisor processor 532, for example. Alternatively, the interfaces 520 and 522 may be replaced by nonconfigurable devices that are custom built to perform specific routing tasks (e.g., hard-coded).

The supervisor processor 532 may be configured to route images to the data distributor's lower leaf cluster cards based on any suitable criteria. For example, the images may be divided and routed based on image coordinates, such as column numbers or corresponding sample coordinates. Likewise, the reference data may be routed based on database addresses within the database storage device 420.

After image interface 520 selects which images to route to its underlying leaf cluster cards, the selected images may be routed to one or more LCC modules 502. In one embodiment, the data distributor 406 is arranged to interface with a plurality of leaf cluster cards. Hence, the data distributor 406 includes a number of LCC modules 502 for interfacing with each leaf cluster cards. For example, if the data distributor interfaces with eight leaf cluster cards, it will include eight LCC modules 502. Each LCC module may include a buffer 528 for holding image data, a buffer 510 for holding data and control information, and an LCC interface 506 for communicating with the associated leaf cluster card.

As shown, the image data is routed to buffer device 528. The buffer 528 may be any suitable size for storing the image data. In one embodiment, the buffer 528 is in the form of a FIFO and stores enough images for eight leaf cluster cards. For example, the image buffer 528 may provide up to 512 megabytes of data. Thus, the total memory in all of the data distributor image buffers 528 may be larger then the full size of a swath of image data.

Likewise, after database and control interface 522 selects which reference images and control data to route to its underlying leaf cluster cards, the selected data may be routed to one or more LCC modules 502. As shown, the database and control data is routed to buffer device 510 of a selected LCC module 502. The buffer 522 may be any suitable size for storing the database and control data.

Each LCC interface 506 (or LCC module 502) is configured to respond to data requests from its associated leaf cluster card. That is, the LCC interface 506 retrieves data from the buffers 520 and 522 when the associated leaf cluster card requests it. After receiving a request for data, LCC interface block 506 forwards a portion of the image data to the requesting leaf cluster card. The forwarded data may then be processed by one or more of the associated leaf processors of the associated leaf cluster card.

Figure 6:
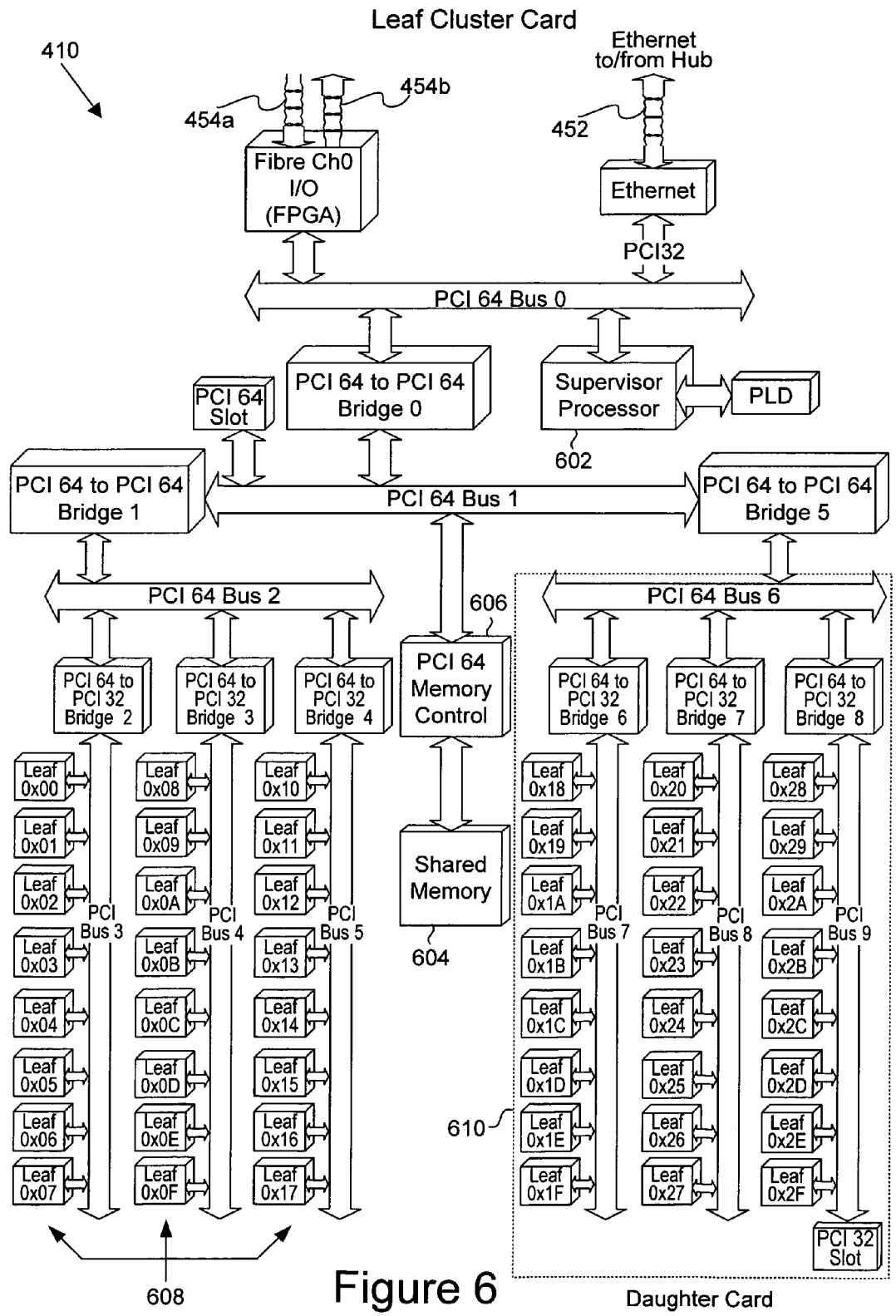
FIG. 6 is a diagrammatic representation of one of the leaf cluster cards of FIG. 4 in accordance with one embodiment of the present invention.

FIG. 6 is a diagrammatic representation of one of the leaf cluster cards 410 of FIG. 4 in accordance with one embodiment of the present invention. As shown, the leaf cluster card 410 includes a plurality of processors 608 (herein referred to as "leaf processors"). In the illustrated embodiment, the leaf cluster card 410 includes 48 individual leaf processors. Along with the 48 processors, the leaf cluster card 410 also includes a shared memory pool 604 and a supervisor processor 602.

Image data and database data is received through input 454*a*. Result data may be output through interface 454*b*. Supervisor processor 602 may be accessed and configured through network interface 452.

The supervisor processor 602 may be programmed to carry out a plurality of suitable tasks to facilitate analysis of the images. For example, the supervisor processor 602 may be responsible for determining which data (e.g., which image and reference data) is routed to which individual processor 608. For example, a image and corresponding reference data portion may be routed to one of the leaf processors (608) for comparison of the image and reference data.

Additionally, one or more algorithms may be assigned for each image. In one embodiment, the supervisor processor 602 receives a job set that specifics which job or set of algorithms will be implemented on which images. The supervisor processor 602 may then access the appropriate job set and determine which algorithms and reference data will be implemented for a particular image. The appropriate image, reference data, and job set may then be routed to a leaf processor 608. Each leaf job may include information that is suitable for processing particular images. Thus, each job may include one or more algorithms, for example, for implementing on a particular image, as well as data and instructions necessary for implementing the algorithm(s).

Figure 7:
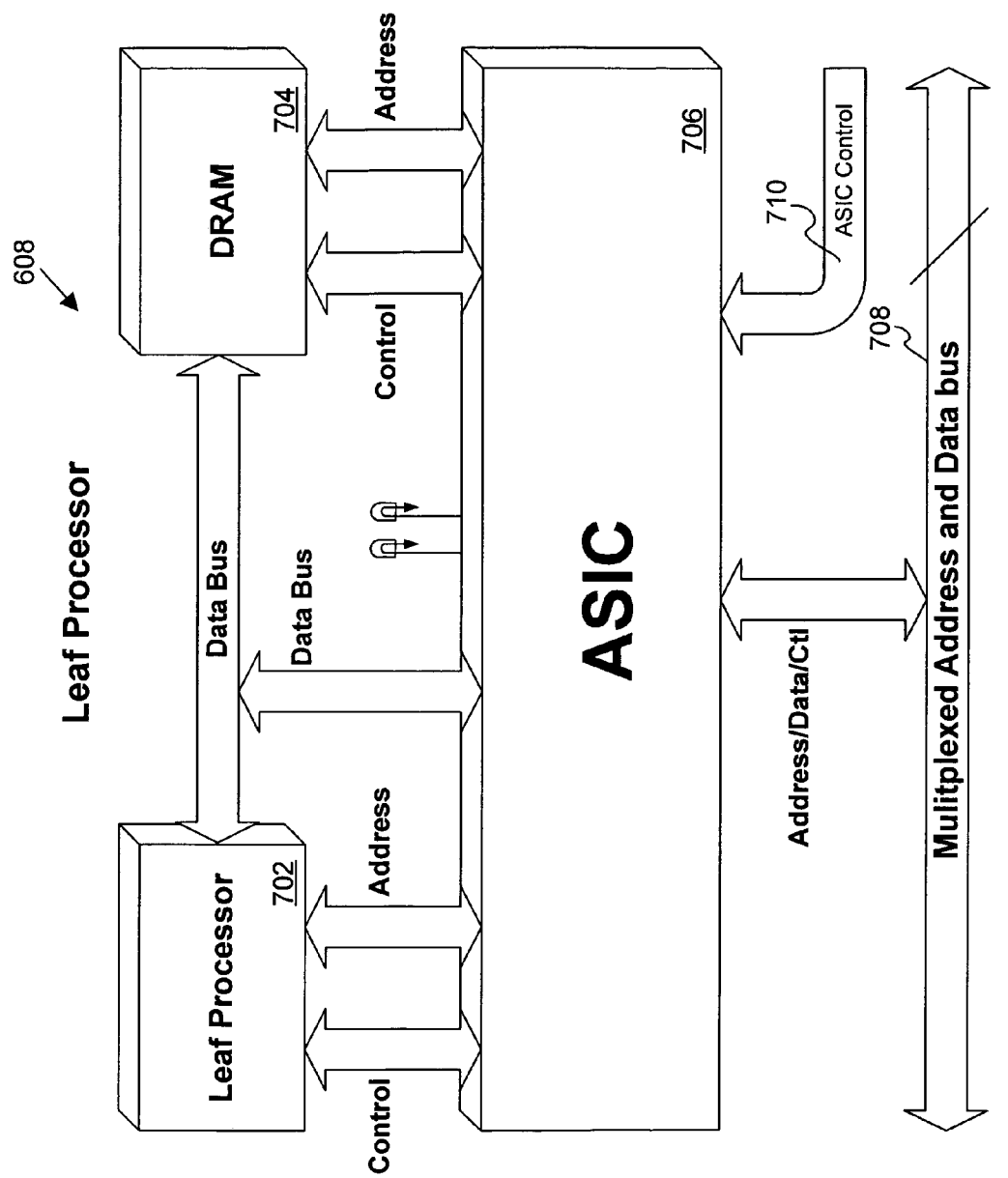
FIG. 7 is a diagrammatic representation of a single leaf processor of FIG. 6 in accordance with one embodiment of the present invention.

FIG. 7 is a diagrammatic representation of a single leaf processor 608 of FIG. 6 in accordance with one embodiment of the present invention. As shown, the leaf processor 608 includes the actual leaf processor 702, one or more memory devices 704, and an interface integrated circuit 706 (e.g., Application Specific Integrated Circuit (ASIC) device). The leaf processor may take any suitable form for processing image data. For example, Intel StrongARM™ processors may be implemented. The memory devices 704 may take any suitable form for storing information necessary for processing the image data. For example, the memory devices 704 may include two DRAM devices and a ROM device. The bus interface device 706 may take any suitable form for communication with the supervisor processor 602 of a leaf cluster card 410. For example, if a PCI bus is used between the supervisor processor 602 and the various processors, an ASIC may be implemented that is configured to interface with a PCI bus.

Preferably, each processor of the leaf cluster card has its own local memory for storing programming instructions. Ideally, the processors operate independently with no sharing of information. Thus, if a particular processor's locally stored instructions are corrupted, other processors can continue to use their own uncorrupted instructions.

In one embodiment, when a processor (e.g., 608) of the leaf cluster card becomes available, it polls the supervisor processor 602 to indicate that it is available for receiving an image, corresponding database data, and a corresponding job set. Each time the supervisor receives an image, it routes the received image to a processor based on which processors have indicated that they are available. Routing may also be based on other suitable factors, such as load balancing considerations.

In a preferred embodiment, the present invention has several advantages. For example, it provides mechanisms for reliably processing image data since a processor of the leaf cluster card may fail and other processors may then take over processing. That is, when a particular processor is down, other processors will poll the supervisor processor 602 to indicate when they are available. Thus, the supervisor processor 602 may simply route images to other available processors thereby bypassing any failed processors.

Figure 8:
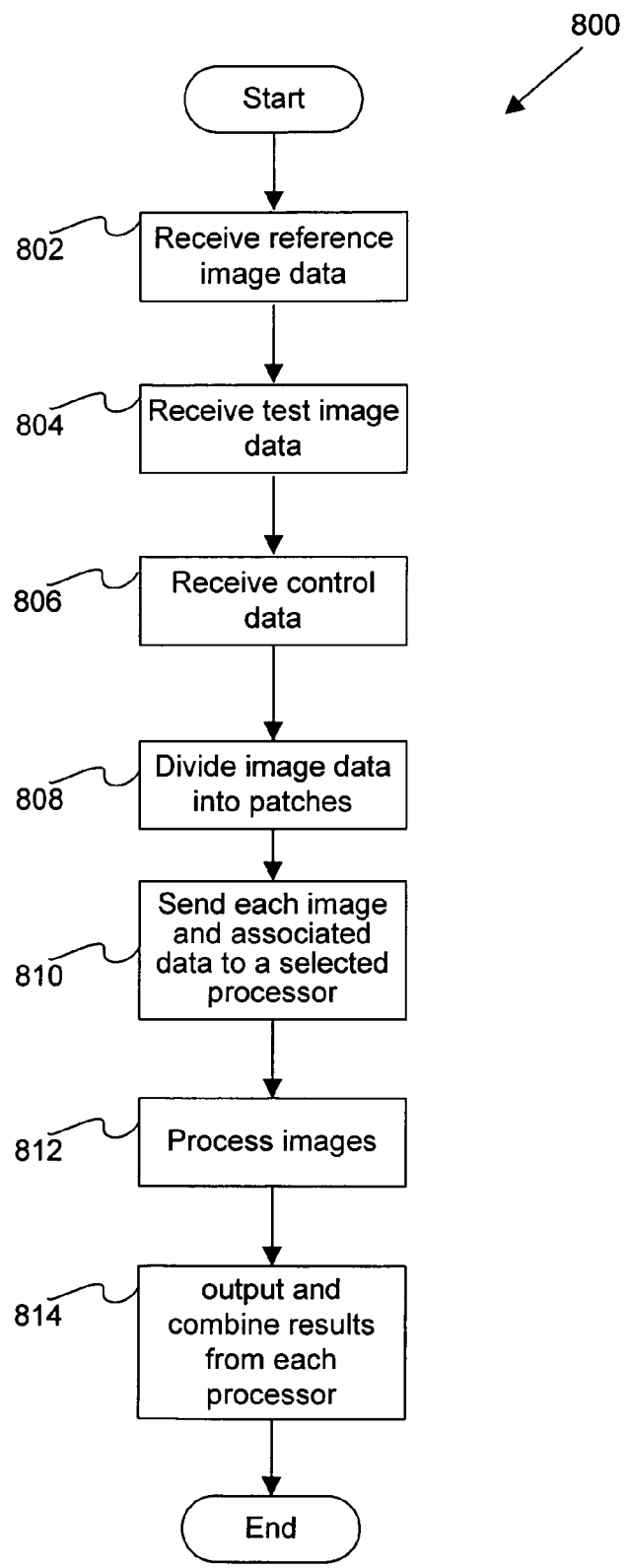
FIG. 8 is a flow diagram illustrating a process for analyzing image data in accordance with one embodiment of the present invention.

FIG. 8 is a flow diagram illustrating a process 800 for analyzing image data in accordance with one embodiment of the present invention. Although FIG. 8 is presented as a series of sequential operations, of course, two or more operations of this process may be implemented in parallel. Additionally, the operations may be performed in any suitable order, besides the order represented in FIG. 8.

Reference image data is received in operation 802. As described above, the reference image data may take any suitable form for facilitating analysis of the received image data. The reference image data may be rendered by any of the processors of the present invention. For example, the processors that analyze the test image data (e.g., compare the test image data to the reference image data) may also render the reference image data. Alternatively, the processors that distribute the test image data (e.g., within the data distributors) may also render the reference image data.

Test image data is also received in operation 804. As described above, this image data 802 is received from any suitable image acquisition system configured for obtaining an image of a sample. The test image data 802 is received by a first group of supervisor processors (e.g., within the data distributors).

Other control data for facilitating image analysis is also received in operation 806. This control data may include information for performing tasks on the received test image data or on each test image. For example, each test image may be associated with a specific job set that specifies how to analyze the associated test image. The control data may also include commands for routing the test images to specific processors, algorithms and associated data for analyzing each test image, and commands that indicate how to divide the test image data into test images or test image portions. The test image data, reference image data, and control data may be received in any order by the first group of processors. Alternatively, any portion of control data may be received directly by a second group of processors that perform the actual image analysis.

After the necessary data is received, in operation 808, the test image data is divided into test images based on the received control data. For example, the control data may indicate which columns of pixels are to be defined as which test images. After the test image data is divided into a plurality of test images, each of the test images and associated job set are sent to a selected processor in operation 810. Each test image may be defined and routed to its appropriate processor as soon as the test image is defined or after all of the test images are defined. Operation 810 may implemented by one or more processors, e.g., the supervisor processors of the data distributors.

After a test image is routed to a processor, the processor may analyze the received test image in operation 812. The test images may be analyzed in parallel, or on a "first come, first served" basis, for example. In other words, the processors are configured to operate in parallel, but test images may be routed together or one at a time, as well as together, to the individual processors. Likewise, processing may begin after all of the processors receive their test images and corresponding data, or each processor may begin analysis as soon as a test image and corresponding data is received.

As the test images are analyzed, results may be output and collected. The results may be collected in any suitable storage device, such as within a "results file" or "results database". After all of the test images are analyzed, the results may be reviewed for the entire set of test image data. Alternatively, portions of the results data may be reviewed as analysis for the particular portion is completed. The results may be reviewed in any suitable manner. For example, the results may be presented through a graphical user interface that presents the data in meaningful ways, such as bar graphs. After the results are collected for an image data set, the process 800 for analyzing image data ends.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. For example, although the present invention has been implemented with a local area network (e.g., Ethernet), of course, it may implemented on a wide area network, such as over the Internet or a bus, such as VME bus.

Accordingly, the present embodiments are to be considered as illustrative and not restrictive, and the invention is not to be limited to the details given herein, but may be modified within the scope and equivalents of the appended claims.

What is claimed is:

1. An apparatus for inspecting a plurality of image portions of at least a region of a sample for defects, the apparatus comprising:

a plurality of processors arranged to receive and analyze the image portions, the processors being arranged to operate in parallel and being configurable to implement one or more algorithms selected from a plurality of different algorithms for analyzing the image portions to determine whether the corresponding regions of the sample are defective, wherein each processor has access to a memory portion sized to hold at least one of the image portions; and a data distribution system arranged to receive image data, select at least a first processor for receiving a first image portion and not a second image portion of the image data and one or more first algorithms selected from the plurality of different algorithms, select at least a second processor for receiving the second image portion and not the first image portion of the image data and one or more second algorithms selected from the plurality of different algorithms, output the first image portion to the memory portion that is accessible by the first processor and the second image portion to the memory portion that is accessible by the second selected processor, and configure the first processor with the one or more first algorithms and the second processor with the one or more selected algorithms, wherein the first image portion and the second image portion are different rectangular shaped image portions that each has a width that comprises a plurality of pixels and a length that comprises a plurality of pixels, wherein the first processor is then operable to implement the one or more first algorithms to analyze substantially all of the first image portion to determine whether the analyzed first image portion has a defect and the second processor is then operable to implement the one or more second algorithms to analyze substantially all of the second image portion to determine whether the analyzed second image portion has a defect, when the defect determination operations for the first and second image portions are each based on analysis of substantially all of the respective image portion.

2. An apparatus as recited in claim 1, wherein the data distribution system is further arranged to divide the image data into a plurality of image portions.

3. An apparatus as recited in claim 1, wherein the first processor is arranged to receive a first reference image portion corresponding to the first image portion and to compare the first image portion to the first reference image portion, and the second processor is arranged to receive a second reference image portion corresponding to the second image portion and to compare the second image portion to the second reference image portion, and wherein determining whether the analyzed first image portion has a defect is based on the comparison between the first image portion and the first reference image portion and determining whether the analyzed second image portion has a defect is based on the comparison between the second image portion and the second reference image portion.

4. An apparatus as recited in claim 3, wherein the first reference image portion is derived from a corresponding portion of the sample.

5. An apparatus as recited in claim 3, wherein the first reference image portion is derived from a file used to design the sample.

6. An apparatus as recited in claim 1, wherein at least a part of the first image portion is identical to at least part of the second image portion.

7. An apparatus as recited in claim 1, wherein the first processor is configured with a different algorithm for analyzing the first image portion than the second processor.

8. An apparatus as recited in claim 1, wherein the first processor is arranged to receive a first reference data portion that characterizes a pattern in the sample that the first image portion corresponds to, and the first processor is also arranged to render the first reference data portion to a first reference age portion and to compare the first reference image portion to the first image portion.

9. An apparatus for inspecting a plurality of image portions of at least a region of a sample, the apparatus comprising:
a plurality of distributors arranged to receive the image portions; and
a plurality of processors that are arranged into a plurality of subgroups that are each coupled to an associated distributor, wherein each processor has access to a memory portion sized to hold at least one of the image portions, each processor being configurable to implement one or more algorithms selected from a plurality of different algorithms for analyzing the image portions to determine whether the corresponding regions of the sample are defective, each distributor being configurable to select one or more algorithms selected from the plurality of different algorithms, output selected image portions to its associated subgroup of processors whereby a different set of one or more image portions is output to each associated processor's accessible memory portion and configure each processor with its selected one or more algorithms, at least two of the processors being arranged to analyze at least two of the image portions in parallel, wherein the image portions are different rectangular shaped image portions that each has a width that comprises a plurality of pixels and a length that comprises a plurality of pixels, wherein each of the at least two processors are operable to implement its selected one or more algorithms to substantially all of each of its image portions to determine whether the analyzed each image portion has a defect.

10. An apparatus as recited in claim 9 wherein the distributors are arranged in a daisy chain configuration such that a first distributor receives the image portions and outputs one or more of the image portions to a second distributor.

11. An apparatus as recited in claim 9 wherein each subgroup of processors includes a supervisor processor that is coupled with an associated one of the distributors so as to receive the selected image portions from the associated distributor, wherein each supervisor processor is configurable to distribute the selected image portions to selected processors within its associated subgroup.

12. An apparatus as recited in claim 9 wherein a first processor is arranged to receive a selected image portion and a selected reference image portion corresponding to the selected image portion and to compare the selected image portion to the selected reference image portion.

13. An apparatus as recited in claim 12, wherein the selected reference image portion is derived from a corresponding portion of the sample.

14. An apparatus as recited in claim 9, wherein a first processor is arranged to receive a selected image portion and a reference data portion that characterizes a pattern of the sample that the selected image portion corresponds to, the first processor being further arranged to render a reference image portion from the reference data portion and to compare the reference image portion to the selected image portion.

15. An apparatus as recited in claim 14, wherein the reference data portion is derived from a file used to design the sample.

16. A method of inspecting a sample having a plurality of fine patterns thereon, and processing data resulting from the inspection, comprising:

a) receiving data derived from the inspection in a multi-processor system, the system comprising a master processor and a plurality of slave processors;
b) dividing the data into groups using the master processor and sending a different data group to a different memory portion that is accessible by a different one of the slave processors, each data group corresponding to information derived from a portion of the sample, wherein the data groups are different rectangular shaped image portions that each has a width that comprises a plurality of pixels and a length that comprises a plurality of pixels, wherein each slave processor is configurable to implement one or more algorithms selected from a plurality of different algorithms for analyzing substantially all its received data group to determine whether the corresponding portion of the sample is defective;
c) selecting one or more algorithms from the plurality of different algorithms for each slave processor and configuring each slave processor with the selected one or more algorithms for such each slave processor;
d) processing the data groups with the slave processors based on the selected one or more algorithms for each slave processor; and
e) deriving defect information regarding the sample and the fine patterns from the combined data.

17. The method of claim 16, wherein the sample is selected from a group consisting of a reticle, a photomask, and a semiconductor material, device, or surface.

18. The method of claim 16, wherein the system comprises a plurality of master processors, each in communication with a plurality of slave processors, and wherein each of the master processors is in communication with a central processor, the central processor allocating data among the master processors.

19. The method of claim 16, wherein a first group of the slave processors uses one or more algorithms selected to process data with high accuracy, but at a relatively slow rate, and wherein a second group of the slave processors uses one or more algorithms selected to process data with a relatively low accuracy, but at a high rate.

20. The method of claim 16, where the data groups are processed using an algorithm which compares data derived from differing regions of the sample.

21. The method of claim 16, wherein the data groups are processed using an algorithm which compares data derived from a portion of the sample with data derived from a file used to design the sample.

22. A method for analyzing image data obtained from a sample using a plurality of processors, comprising the acts of:
receiving image data from an inspection system that generates the image data from a sample;
dividing the image data into a plurality of image portions that correspond to various portions of the sample;
outputting each image portion to a memory portion that is accessible by a selected processor, at least some of the image portions going to different memory portions that are accessible by different processors, each processor being configurable to implement one or more algorithms selected from a plurality of different algorithms for analyzing the image portions to determine whether the corresponding portions of the sample are defective, wherein the image portions are different rectangular shaped image portions that each has a width that comprises a plurality of pixels and a length that comprises a plurality of pixels;

selecting one or more algorithms from the different algorithms of each selected processor and configuring each selected processor with its selected one or more algorithms;

analyzing substantially all of each image portion for defects within the selected processor based on the selected one or more algorithms for such selected processor to then determine whether the corresponding portion of the each analyzed image portion has a defect; and outputting and combining results from each processor such that defect data is compiled for the entire image data.

23. A method as recited in claims 22, wherein at least some of the image portions are analyzed with different algorithms.

24. A method as recited in claims 22, wherein at least some of the image portions are analyzed more stringently than others of the image portions.

25. A method as recited in claims 22, further comprising receiving reference data corresponding to each image portion.

26. A method as recited in claims 25, wherein each image portion is analyzed by comparing each image portion to its corresponding reference data.

27. A method as recited in claims 25, wherein the reference data is in form of a corresponding image portion of the sample.

28. A method as recited in claims 25 wherein the reference data is in form of design data that is used to contact the sample.

29. A method as recited in claims 22 further comprising receiving control data that specifies how to divide and output the image portions to their selected processors.

30. A method as recited in claims 29 wherein the control data also specifies how to analyze the image portions for defects within the selected processors.

31. A method as recited in claims 30 wherein the reference data is in form of design data that is used to construct the sample, and the control data also specifies how to render the reference data from the design data.

32. A computer readable medium containing program instructions for inspecting a sample having a plurality of fine patterns thereon, and processing data resulting from the inspection, the computer readable medium comprising:

computer readable code for receiving data derived from the inspection in a multiprocessor system, the system comprising a master processor and a plurality of slave processors; computer readable code for dividing the data into groups using the master processor and sending a different data group to a different memory portion that is accessible by a different one of the slave processors, each data group corresponding to information derived from a portion of the sample, wherein the data groups are different rectangular shaped image portions that each was a width that comprises a plurality of pixels and a length that comprises a plurality of pixels, wherein each slave processor is configurable to implement one or more algorithms selected from a plurality of different algorithms for analyzing substantially all its received data group to determine whether the corresponding portion of the sample is defective computer readable code for selecting one or more algorithms from the plurality of different algorithms for each slave processor and configuring each slave processor with the selected one or more algorithms for such each slave processor;

computer readable code for processing the data groups with the slave processors based on the selected one or more algorithms for each slave processor, computer readable code for deriving defect information regarding the sample and the fine patterns from the combined data; and a computer readable medium for storing the computer readable codes.

33. A computer readable medium as recited in claim 32, wherein each of the plurality of master processors is in communication with the plurality of slave processors, and wherein each of the master processors is in communication with a central processor, the central processor allocating data among the master processors.

34. A computer readable medium as recited in claim 32, wherein a first group of the slave processors uses one or more algorithms selected to process data with high accuracy, but at a relatively slow rate, and wherein a second group of the slave processors uses one or more algorithms selected to process data with a relatively low accuracy, but at a high rate.

35. A computer readable medium as recited in claim 32, wherein the data groups are processed using an algorithm which compares data derived from differing regions of the sample.

36. A computer readable medium as recited in claim 32, wherein the data groups are processed using an algorithm which compares data derived from a portion of the sample with data derived from a file used to design the sample.

37. A computer readable medium containing program instructions for inspecting a sample having a plurality of fine patterns thereon, and processing data resulting from the inspection, the computer readable medium comprising:

computer readable code for receiving image data from an inspection system that generates the image data from a sample;

computer readable code for dividing the image data into a plurality of image portions that correspond to various portions of the sample;

computer readable code for outputting each image portion to a memory portion that is accessible by a selected processor, at least some of the image portions going to different memory portions that are accessible by different processors, each processor being configurable to implement one or more algorithms selected from a plurality of different algorithms for analyzing the image portions to determine whether the corresponding portions of the sample are defective, wherein the image portions are different rectangular shaped image portions that each has a width that comprises a plurality of pixels and a length that comprises a plurality of pixels;

computer readable code for selecting one or more algorithms from the different algorithms of each selected processor and configuring each selected processor with its selected one or more algorithms;

computer readable code for analyzing substantially all of each image portion for defects within the selected processor based on the selected one or more algorithms for such selected processor to then determine whether the corresponding portion of the each analyzed image portion has a defect; and computer readable code for outputting and combining results from each processor such that defect data is compiled for the entire image data; and a computer readable medium for storing the computer readable codes.

38. A computer readable medium as recited in claims 37, wherein at least some of the image portions are analyzed more stringently than others of the image portions.

39. A computer readable medium as recited in claims 37, further comprising computer readable code for receiving reference data corresponding to each image portion.

40. A computer readable medium as recited in claims 39, wherein each image portion is analyzed by comparing each image to its corresponding reference data.

41. A computer readable medium as recited in claims 39, wherein the reference data is in form of a corresponding image portion of the sample.

42. A computer readable medium as recited in claims 39, wherein the reference data is in form of design data that is used to construct the sample.

43. A computer readable medium as recited in claims 37, further comprising computer readable code for receiving control data that specifies how to divide and output the image portions to their selected processors.

44. A computer readable medium as recited in claims 43, wherein the control data also specifies how to analyze the image portions for defects within the selected processors.

45. A method as recited in claims 44 wherein the reference data is in form of design data that is used to construct the sample, and the control data also specifies how to render the reference data from the design data.

* * * * *

UNITED STATES PATENT AND TRADEMARK OFFICE
CERTIFICATE OF CORRECTION

PATENT NO. : 7,106,895 B1  Page 1 of 1
APPLICATION NO. : 09/449022
DATED : September 12, 2006
INVENTOR(S) : Goldberg et al.

It is certified that error appears in the above-identified patent and that said Letters Patent is hereby corrected as shown below:

In the Title Page:

Add the following priority information data:

-- Related U.S. Application Data
(60)  Provisional application no. 60/132,872, filed on May 5, 1999. --

SPECIFICATION:

Column 1, before line 5, add -- The present application claims priority under 35 U.S.C. 119(e) to U.S. Provisional Patent Application No. 60/132,872 (Attorney Docket No. KLA1P007P), filed May 5, 1999. --

Signed and Sealed this

First Day of January, 2008

JON W. DUDAS
*Director of the United States Patent and Trademark Office*